United States Patent [19]

Christensen et al.

[11] Patent Number: 4,988,807

[45] Date of Patent: Jan. 29, 1991

[54] REMOVAL OF UNDESIRABLE MATERIAL FROM WATER-SOLUBLE POLYSACCHARIDE ETHERS

[75] Inventors: Stephen B. Christensen; Gary J. Schulz; Susan Kling, all of Midland, Mich.

[73] Assignee: The Dow Chemical Company, Midland, Mich.

[21] Appl. No.: 506,724

[22] Filed: Apr. 9, 1990

Related U.S. Application Data

[63] Continuation-in-part of Ser. No. 300,666, Jan. 23, 1989, abandoned.

[51] Int. Cl.$^5$ .............................................. B01D 15/04
[52] U.S. Cl. .................................... 536/127; 210/692; 210/917
[58] Field of Search ............... 210/683, 686, 692, 917; 536/85, 91, 95, 96, 99, 100, 127

[56] References Cited

U.S. PATENT DOCUMENTS 4,454,045  6/1984  Perplies .............................. 210/672

OTHER PUBLICATIONS

Derwent Publication 100224b, 1970, 23(5), Glazman et al., Use of an Ion-Exchange Resin for Clarifying Pentosan Hydrolyzates of Corncobs.

Primary Examiner—Ivars Cintins

[57] ABSTRACT

A method of removing undesirable material from water-soluble polysaccharide ethers, such as water-soluble cellulose ethers, via contact of an aqueous solution of the water-soluble polysaccharide ether with an anion exchange resin. Anion exchange resins that are useful in the invention are derived from epoxy resin polymers, acrylic based copolymers or a copolymer of styrene-divinylbenzene. The method significantly reduces the amount of colored bodies in the polysaccharide ether.

17 Claims, No Drawings

REMOVAL OF UNDESIRABLE MATERIAL FROM WATER-SOLUBLE POLYSACCHARIDE ETHERS

CROSS REFERENCE TO RELATED APPLICATION

This is a continuation-in-part of copending U.S. Application Ser. No. 07/300,666, filed Jan. 23, 1989.

BACKGROUND OF THE INVENTION

This invention pertains to the removal of undesirable material, particularly color bodies, from water-soluble polysaccharide ethers.

Water-soluble polysaccharide ethers are used for their many different properties and are employed in a variety of applications. The polysaccharide ethers are used as thickeners, binders, film formers, water-retention aids, suspension aids, surfactants, lubricants, protective colloids, emulsifiers, and the like, and are used in applications such as foods, cosmetics, pharmaceuticals, latex paints, construction products, ceramics, and a host of other applications. A problem encountered by those that produce and consequently those that use the water-soluble polysaccharide ethers is the presence of contaminants, such as undesirable color and salt. The undesirable color contamination is of particular concern to the pharmaceutical industry.

The color in water-soluble polysaccharide ethers and, in particular, water-soluble cellulose ethers, can vary from a very pale-yellow to a golden or even brown hue, depending on the level of color bodies in the product. For some applications the presence of this color is not a problem, but for other applications, in particular tablet coating in the pharmaceutical industry, the colorant causes difficulties. It would be desirable to have a method of removing or reducing the residual color for those applications in which low levels of the color are required.

SUMMARY OF THE INVENTION

This invention is a process for removing the undesirable material from water-soluble polysaccharide ethers containing such undesirable material by contacting an aqueous solution of such water-soluble polysaccharide ethers with an anion exchange resin. The process comprises using an anion exchange resin in an amount and at conditions effective to associate the undesirable material with the resin and to separate the resin from the polysaccharide ether so as to result in a polysaccharide ether having a reduced concentration of undesirable material.

This invention can be used to decolorize, or reduce the color of, water-soluble polysaccharide ethers, such as water-soluble cellulose ethers, containing undesirable color bodies. In particular, the invention has proven useful in decolorizing water-soluble polysaccharide ethers that are used in the pharmaceutical industry. The process can also be used to decolorize water-soluble polysaccharide ether material that has been recovered by ultrafiltration of process wash streams during the manufacture of the water-soluble polysaccharide ethers. Said recovered water-soluble polysaccharide ethers are typically highly colored and some decolorization is necessary to produce an acceptable product. Additionally, this invention can be useful in removing other undesirable material from water-soluble polysaccharide ethers, such as minor amounts of salt.

DETAILED DESCRIPTION

This invention is a process for removing the undesirable material from water-soluble polysaccharide ethers containing such undesirable material via the use of an anion exchange resin.

According to the process of the present invention, the polysaccharide ether containing undesirable material, or a mixture of polysaccharide ethers containing undesirable material, is mixed with an aqueous solvent to form an aqueous solution before contact with the anion exchange resin. As such, the polysaccharide ethers useful in the present invention are those that are soluble in water. Preferably, the aqueous solvent is simply water, although an aqueous solvent which is up to about 20 weight percent alcohol can also be used, depending on the particular water-soluble polysaccharide ether to be treated in the process.

In the present specification and claims, the term "undesirable material" is meant to represent contaminants such as color bodies and salt, as well as other contaminants that interfere with the desired use of the water-soluble polysaccharide ether.

Polysaccharide ethers are the etherified products of a polysaccharide. Representative polysaccharides include: cellulose; natural gums such as arabic, xanthan, and guar; dextran; and starch. Cellulose is the preferred polysaccharide. Examples of such ethers can include cellulose ethers such as alkylcellulose or hydroxyalkyl alkylcellulose, methylcellulose, hydroxypropyl methylcellulose, hydroxyethyl methylcellulose, ethyl methylcellulose, hydroxyethyl hydroxypropyl methylcellulose, hydroxyethylcellulose, and hydroxypropylcellulose.

By "anion exchange resin" is meant a solid polymeric material that has a positively charged matrix and exchangeable negative ions or anions.

Anion exchange resins that are useful in the invention herein are functionalized copolymer beads or copolymer beads that have been pulverized. Preferably, the anion exchange resin is employed in the bead form of the resin. The polymer beads from which anion exchange resins are derived can be prepared from epoxy resin-based polymers, (e.g., an epoxy-amine polymer); acrylic copolymers (e.g., an acrylic-divinylbenzene copolymer); and copolymer compositions of styrene-divinylbenzene. Anionic exchange resins are typically prepared via suspension polymerization of comonomers and are then functionalized with groups that can exchange anions. To functionalize the copolymer beads, the beads can be chloromethylated with chloromethylmethylether (CMME) and then aminated with a dimethylamine to provide weak-base functionality or a trimethylamine to provide a strong-base functionality.

Another useful resin which could be employed in the invention herein is an adsorptive, porous, post-crosslinked resin in bead form. The adsorptive, porous post-crosslinked resin is prepared by contacting a functionalized resin in a swollen state with a Friedel-Craft catalyst under conditions effective to catalyze the post-crosslinking and rearrangement of the swollen functionalized resin. Examples of these polymeric post-crosslinked absorbent resins are taught in U.S. Pat. No. 4,263,407.

The anion exchange resin useful in the invention herein typically has a substituent that is either a strong-base quaternary ammonium group or a weak-base amino group. If the substituent is an alkyl quaternary ammonium salt, the material is known in the industry as a strong-base anion exchange resin. If the substituent is an amine or alkyl amine group, the material is known as a weak-base resin. The weak-base resins are effective in the unaltered or free-base form; whereas, the strong-base resin is effective with a chloride or hydroxide counterion, also known in the ion exchange art as the chloride or hydroxide ion form.

It has also been found useful to use the ammonium salt form of the weak-base resin which is formed by the interaction of a weak-base resin with any suitable mineral acid. The mineral acids could include hydrochloric acid and sulfuric acid, with hydrochloric acid being preferred.

While any anion exchange resin will serve to reduce the color of the water-soluble polysaccharide ethers containing undesirable color bodies, preferably the resin has a large internal pore size. Thus, generally a macroporous resin is to be preferred over a gel-type resin. Generally, suitable resins usually have a styrene-divinylbenzene matrix, such as DOWEX® SBR-P (a Trademark of The Dow Chemical Company), a strong-base gel resin; DOWEX® 11, a strong-base gel resin; DOWEX® MWA-1, a weak-base macroporous resin; and DOWEX® MSA-1, a strong-base macroporous resin.

Other suitable resins could include the following resins: a resin having a styrene-divinylbenzene matrix, e.g., AMBERLITE® IRA-93 (a trademark of Rohm and Haas Company), a weak-base macroreticular styrene-divinylbenzene resin; an acrylicdivinylbenzene matrix, e.g., AMBERLITE® IRA-958, a strong-base macroreticular acrylic-divinylbenzene resin; an epoxy resin-based polymer, e.g., DOWEX® WGR-2, an intermediate base resin with an epoxy amine matrix. Of course, there are many equivalents for all of these resins. The preferred resins of this invention are the DOWEX® MWA-1, a weak-base macroporous resin, and the DOWEX® MSA-1, a strong-base macroporous resin.

In addition to using particular anionic resins, some of which are described hereinabove, mixed bed resins can also be useful in the invention. Such a suitable resin is DOWEX® MR-3, a combination of a strong-base gel styrene-divinylbenzene resin and a strong acid cation exchange styrene-divinylbenzene resin.

If the anion exchange resin is a strong-base resin or the ammonium salt of a weak-base resin, then a counterion or anion will be present in the system. This counterion may be a chloride, hydroxide, or sulfate anion. In decolorizing water-soluble polysaccharide ethers containing undesirable color bodies in aqueous solutions in which high pH levels are to be avoided, chloride is the preferred anion. The chloride ion is preferred since it is most commonly found in these water-soluble polysaccharide ether aqueous solutions. Use of a strong-base resin with the hydroxide counterion in situations where demineralization as well as color removal are desired allows the hydroxide counterion in the anion exchange column to also function as one-half of a two-stage desalting process. This eliminates the need for an additional anion exchange column.

To remove the undesirable material from the water-soluble polysaccharide ether containing such undesirable material, e.g., color, salt, and the like, a column is first packed with an anion exchange resin and then washed with water. If necessary, the column may then be converted into the proper anionic form by treatment with the appropriate solution. For instance, pretreatment of a strong-base resin could be performed by passing any of the following solutions down the column: 4 percent sodium hydroxide solution to give the hydroxide form of the resin; 15 percent sodium chloride solution to give the chloride form of the resin; 6 percent hydrochloric acid solution to give the chloride form of the resin; and 4 percent sulfuric acid to give the sulfate form of the resin.

To convert the column to the proper ionic form using a weak-base resin, the following solutions could be washed down the column: 6 percent hydrochloric acid solution to give the ammonium chloride salt form of the resin and 4 percent sulfuric acid solution to give the ammonium sulfate salt form of the resin. These values are given only as examples and are not meant to be limiting. The column is then washed with water to remove excess ions.

Finally, the water-soluble polysaccharide ether containing undesirable material, in an aqueous solution, is passed down the column at such a flow rate that the desired level of undesirable material is achieved. The anion exchange resin is used in an amount and at conditions effective to associate the undesirable material with the resin resulting in a water-soluble polysaccharide ether having a reduced concentration of undesirable material. Subsequent to the treatment of the water-soluble polysaccharide ether aqueous solution, the purified water-soluble polysaccharide ether is typically recovered from the aqueous solution and collected as a dry product.

In the present specification and claims, the term "associate" is meant to represent the adsorption or ionic bonding of the undesirable material with the anion exchange resin such that the undesirable material is removed from the polysaccharide ether by the anion exchange resin when an aqueous solution of the polysaccharide ether is contacted with the anion exchange resin.

The flow rate of the process and the size of the column to be used are a function of: the amount of undesirable material in the polysaccharide ether, the resin being used, and the amount of undesirable material to be removed. The exact values for each of these parameters must be adjusted to meet the desired results. In general, the amount of removal of undesirable material is a function of the contact time of the water-soluble polysaccharide ether aqueous solution with the resin, with longer contact times given to more highly purified, water-soluble, polysaccharide ethers. For a given amount of removal of undesirable material, the required contact time can be achieved by numerous combinations of flow rate and column size. Typically, the flow rates range from about 0.001 to about 10.0 gallons per minute per square foot of resin, (gpm/sq ft.), preferably from about 0.1 to about 1.5 gpm/sq ft.

The acceptable level of undesired material in the water-soluble polysaccharide ether remaining after treatment, or, alternatively, the amount of undesired material to be removed from the water-soluble polysaccharide ether during treatment will depend on the specific end use for which the water-soluble polysaccharide ether is intended. Thus, an effective level of removal of the undesired material will be dictated by specific consumer or industrial need requirements of the final product and, as such, will vary from final product to final product.

The process is typically operated at ambient temperatures of about 15° to about 35° C. Elevated temperatures of about 50° to about 60° C. are effective, but at higher temperatures some of the water-soluble polysaccharide ether may precipitate or gel. This gelling or precipitation would cause the column to be blocked; thereby, inhibiting the flow of the aqueous solution through the column. In instances where one would not be concerned with the water-soluble polysaccharide ether gelling, elevated temperatures are workable.

Several factors may effect the efficiency of the removal of undesirable material from the water-soluble polysaccharide ether containing such undesirable material, with the main concerns being the viscosity, pH, and salt content of the water-soluble polysaccharide ether aqueous solution. The water-soluble polysaccharide ether aqueous solution should not be so viscous that reasonable flow rates, as described herein, cannot be achieved without resorting to excess column pressures to force the aqueous solution through the column. Typically accepted pressures to aid in the process are from about 5 to about 300 psig, preferably from about 40 to about 80 psig.

The pH of the water-soluble polysaccharide ether aqueous solution is also a factor in the efficiency of the process. It has been found that if the pH of the aqueous solution is too low the efficiency of the process could be reduced. The pH range necessary for effective removal of undesirable material from the water-soluble polysaccharide ether will be dependent on the specific water-soluble polysaccharide ether to be treated. Additionally, if the resin being used is the ammonium salt of a weak-base resin it is advantageous to keep the pH below about 7 to avoid a rapid deprotonation of the resin by the water-soluble polysaccharide ether aqueous solution. The preferred pH of the polysaccharide ether aqueous solution is therefore generally between about 4 and about 7.

The salt content of the water-soluble polysaccharide ether aqueous solution must be low enough so that the salt does not interfere with the decolorization process. Salt contents as high as 1 to about 2 weight percent are acceptable, with the preferred value being anything below this level. Moreover, this process can be employed to remove minor amounts of salt contained in the water-soluble polysaccharide ether.

When the column's ability to remove the undesirable material is exhausted, or at least the removal is not at the desirable level, then the resin in the column can be regenerated and reused. The first step in the regeneration is to wash the column with water. The column is then treated with any of a variety of agents. The agents have the properties of removing accumulated undesirable material from the resin and restoring the activity of the resin to an effective level. For example, if the undesirable material is color in a water-soluble cellulose ether aqueous solution, a salt solution of about 10 to about 26 weight percent, or either a sodium hydroxide or a mineral acid solution of about 1 to about 10 weight percent, preferably about 2 to about 4 weight percent, can be used to release the accumulated bodies from the column. The preferred regeneration step is to treat the column with a mineral acid, in particular hydrochloric acid. This has the advantage of both regenerating the column and in those cases where a weak-base resin is being used, the acid serves to reprotonate the resin before the next cycle.

Typically, to regenerate the column using the acid, two bed volumes of about 1 to about 10 weight percent hydrochloric acid are pumped through a column over a period of time sufficient to restore the column's efficiency, with about 4 to about 6 weight percent being preferred. This can take from about 45 minutes to about 2 hours. The acid is then purged from the column with fresh water and the column is ready for use again. The regeneration step is normally performed at an ambient temperature. Although, alternatively, elevated temperatures can be used as long as the temperature used does not exceed the upper-temperature limitation of the resin that is employed in the process.

EXAMPLES

Example 1

A 2.5 centimeter (cm) by 30 cm column is packed with resin and used to purify a 10 weight percent, crude hydroxypropyl methylcellulose aqueous solution. This hydroxypropyl methylcellulose has, at 2 weight percent of an aqueous solution, a viscosity of about 5 cps at 20° C. The color of this crude hydroxypropyl methylcellulose aqueous solution, as measured on a Hunter Lab Model D25 Optical Sensor, is a value of 48 APHA units (American Public Health Association) for a filtered 2 weight percent aqueous solution at pH 7. APHA units are determined via use of the Hunter Lab Model D25 Optical Sensor and analysis standards published in Standards Method Manual: Physical, Chemical, Biological analysis of Water-Waste Water, 16th ed., jointly published by the American Public Health Association, the American Water Works Association, and the Water Pollution Control Federation. With this instrument the lower the numerical value the less color that is present in the aqueous solution. For instance, distilled water has a numerical value of zero. Since the color of the hydroxypropyl methylcellulose aqueous solution comes from the hydroxypropyl methylcellulose contained within it, a reduction of the solution color means that the hydroxypropyl methylcellulose has been at least partially decolorized.

The procedure, as herein described above, is carried out for each of several anion exchange resin samples, e.g., A, B, C, ... J. For each of the samples, 120 mL of a resin is placed in the column, then the resin is washed with about two bed volumes (one bed volume equals 120 mL) of water. Any additional column treatments are noted below. The hydroxypropyl methylcellulose aqueous solution is then pumped through the column at a flow rate of about 0.27 gpm/ft². After one hour a sample is collected for 20 minutes. This sample is diluted to a 2 weight percent hydroxypropyl methylcellulose aqueous solution, filtered, adjusted to a pH of 7, and measured for color.

A. DOWEX ® MWA-1, a weak-base macroporous, styrene-divinylbenzene resin, is used in the free-base form.

B. DOWEX ® MWA-1, a weak-base macroporous, styrene-divinylbenzene resin, is used in the ammonium chloride salt form. Before packing the column with the resin, the salt form is made by slurrying the dry resin with 6 percent hydrochloric acid.

C. DOWEX ® MSA-1, a strong-base macroporous styrene-divinylbenzene resin is used, in the hydroxide counterion form. The counterionic form is made by washing the column with 3 bed volumes of 4 percent sodium hydroxide followed by 3 bed volumes of water.

D. DOWEX ® MSA-1, a strong-base macroporous styrene-divinylbenzene resin, is used in the sulfate counterion form. The counterion form is made by washing the column with 3 bed volumes of 6 percent sulfuric acid followed by 3 bed volumes of water.

E. DOWEX® MSA-1, a strong-base macroporous styrene-divinylbenzene resin, is used in the chloride counterion form. The resin is received in the counterion form and is employed as received.

F. AMBERLITE® IRA-93 (a trademark of Rohm and Haas Company), a weak-base macroreticular styrene-divinylbenzene resin, is used in the ammonium chloride salt form. Before packing the column with the resin, the salt form is made by slurrying the dry resin with 6 percent hydrochloric acid.

G. DOWEX® 11, a strong-base gel styrene-divinylbenzene resin, is used in the chloride counterion form. The resin is received in the counterion form and is employed as received.

H. AMBERLITE® IRA-958, a strong-base macroreticular acrylic-divinylbenzene resin, is used in the chloride counterion form. The resin is received in the counterion form and is employed as received.

I. DOWEX® MR-3, a mixed resin bed containing DOWEX® SBR, a strong-base gel styrene-divinylbenzene resin used in the hydroxide counterion form, and DOWEX® HCR-S, a strong acid cation exchange styrene-divinylbenzene resin in the hydrogen counterion form, is received in the counterion form and is employed as received.

J. DOWEX® WGR-2, an intermediate base epoxy amine resin is used in the ammonium chloride salt form. Before packing the column with the resin, the salt form is made by slurrying the dry resin with 6 percent hydrochloric acid.

| Samples | Color APHA units* |
|---|---|
| A | 19 |
| B | 19 |
| C | 19 |
| D | 21 |
| E | 22 |
| F | 23 |
| G | 24 |
| H | 24 |
| I | 25 |
| J | 33 |
| Crude Cellulose Ether Solution | 48 |
| Distilled Water | 0 |

*Color value as measured by a Hunter Lab Model D25 Optical Sensor. The lower the numerical value the less color that is present in the solution.

Results

As is seen in the above table, by running the crude hydroxypropyl methylcellulose aqueous solution down the ion exchange column containing anion exchange resins, colored bodies are removed from the hydroxypropyl methylcellulose. For example, before running the hydroxypropyl methylcellulose aqueous solution down the column, the crude hydroxypropyl methylcellulose aqueous solution has a color value of 48 APHA units; whereas, a sample which has gone through the column containing DOWEX® MWA-1 anion exchange resins has a color value of 19 APHA units (Sample A).

Example 2

A 2-inch diameter × 30 feet long column is filled with Dowex Macroporous MWA-1 resin. The column is backflushed with 50 lbs. of deionized water. The resin is protonated with 40 lbs of 6 percent HCl at about 22 lbs/hr in the up-flow direction. The acid is purged with 50 lbs water at about 22 lbs/hr in the up-flow direction. Then, a 13 percent hydroxypropyl methylcellulose aqueous solution, that has a viscosity of 1.6 cps as a 2 weight percent aqueous solution at 20° C., is recovered from process wash streams by ultrafiltration. The recovered hydroxypropyl methylcellulose aqueous solution is adjusted to a pH value of 5.3 with concentrated HCl. The recovered hydroxypropyl methylcellulose aqueous solution is fed to the column at 1.3 gpm/sq ft (down-flow).

After 110 lbs of hydroxypropyl methylcellulose aqueous solution are pumped through the column, the column is purged with 50 lbs of water, is regenerated with 40 lbs of 6 percent HCl and then purged with 50 more pounds of water (similar to initial conditioning). The column is used again to remove color. This sequence is repeated several times with no loss of column capacity This processing is done at about 25° C.

Results

After the crude hydroxypropyl methylcellulose aqueous solution is run down the column a sample is taken The sample is measured using a Bausch & Lomb Spectronic 20 at 490 nanometers. In the recovered sample 93 percent of the color is removed from the hydroxypropyl methylcellulose aqueous solution, indicating a significant reduction in the color bodies in the hydroxypropyl methylcellulose.

Example 3

A system to both decolorize and deionize a water-soluble cellulose ether containing color bodies and salt is set up consisting of three ion exchange columns in series. Each of the columns has a length to diameter ratio of about 2.5. The first column is packed with DOWEX® MWA-1 weak base anion exchange resin, the second is packed with DOWEX® 550-A strong base anion exchange resin, and the third is packed with DOWEX® 650-C cation exchange resin. The water-soluble cellulose ether to be purified is a hydroxypropyl methylcellulose that has a two weight percent aqueous solution viscosity (Brookfield) of about 3 cps at 20° C., with a neutral two percent aqueous solution color (measured as in Example 1) of about 50 APHA units. The salt (NaCl) content of the hydroxypropyl methylcellulose is determined by titration to be about 0.5 weight percent on a dry weight basis. The powder whiteness of the hydroxypropyl methylcellulose itself is measured using a Hunter Lab Model D25 Optical Sensor set up to measure reflectance from pressed tablets, and calibrated against a standard white tile. By this method, the maximum powder whiteness possible would correspond to a value of about 80 units, with lower numbers representing samples that were less white or more highly colored. The hydroxypropyl methylcellulose to be purified is measured by this method as having a powder whiteness value of about 25.

To purify the hydroxypropyl methylcellulose, an aqueous solution of the hydroxypropyl methylcellulose is first prepared that is about 20 weight percent hydroxypropyl methylcellulose. This hydroxypropyl methylcellulose aqueous solution is then pumped through the three columns in series in the down flow direction at a rate of about 0.1 gallons per minute per square foot of resin. After passing through the columns, the hydroxypropyl methylcellulose is dewatered on a drum dryer.

Results

A sample of purified and dewatered hydroxypropyl methylcellulose is collected and analyzed. The neutral two percent solution color of the purified and dewatered hydroxypropyl methylcellulose is measured as about 15 APHA units. The salt (NaCl) content of the purified and dewatered hydroxypropyl methylcellulose is not detectable (less than 0.01 percent). The powder whiteness value of the purified and dewatered hydroxypropyl methylcellulose is measured as about 65 units.

What is claimed is:

1. A method of removing color bodies from a water-soluble polysaccharide ether containing such color bodies comprising:
    (a) contacting an aqueous solution which comprises a water-soluble polysaccharide ether containing color bodies, with an anion exchange resin in an amount and at conditions effective to associate the color bodies with the resin; and
    (b) separating the resin from the polysaccharide ether so as to result in the polysaccharide ether having a reduced concentration of color bodies;
wherein the water-soluble polysaccharide ether is in the aqueous solution in a concentration greater than about 1 weight percent.

2. The method of claim 1 wherein the anion exchange resin is derived from the group consisting of an epoxy resin polymer, an acrylic based copolymer, and a copolymer composition of styrene-divinylbenzene.

3. The method in claim 2 wherein the epoxy resin polymer is an epoxy-amine copolymer.

4. The method in claim 2 wherein the acrylic based copolymer is an acrylic-divinylbenzene copolymer.

5. The method in claim 1 wherein the anion exchange resin is a weak-base resin.

6. The method in claim 1 wherein the anion exchange resin is a strong-base resin.

7. The method in claim 1 wherein the anion exchange resin is a macroporous resin.

8. The method in claim 1 wherein the anion exchange resin is a gel-type resin.

9. The method in claim 1 wherein the resin is a mixed bed of resins comprising a strong-base styrene-divinylbenzene gel-type resin and a strong-acid cation exchange styrene-divinylbenzene resin.

10. The method in claim 1 wherein the resin is an absorptive, porous, post-crosslinked resin.

11. The method in claim 1 wherein the water-soluble polysaccharide ether is derived from a natural gum.

12. The method in claim 11 wherein the natural gum is selected from the group consisting of arabic, xanthan and guar.

13. The method in claim 1 wherein the water-soluble polysaccharide ether is derived from a dextran.

14. The method in claim 1 wherein the water-soluble polysaccharide ether is derived from a starch.

15. The method of claim 1 wherein the water-soluble polysaccharide ether is a water-soluble cellulose ether.

16. The method of claim 15 wherein the water-soluble cellulose ether is selected from the group consisting of alkylcellulose, hydroxyalkyl alkylcellulose, methylcellulose, hydroxypropyl methylcellulose, hydroxyethyl methylcellulose, ethyl methylcellulose, hydroxyethyl hydroxypropyl methylcellulose, hydroxyethylcellulose, and hydroxypropylcellulose.

17. The method of claim 1 wherein the polysaccharide ether is present in the aqueous solution in a concentration greater than about 5 weight percent.

* * * * *